(12) United States Patent
Zhao et al.

(10) Patent No.: US 8,389,807 B2
(45) Date of Patent: Mar. 5, 2013

(54) METHOD FOR INCREASING EFFICIENCY OF GERMPLASM SCREENING IN PLANT TRANSFORMATION

(75) Inventors: Zuo-Yu Zhao, Johnston, IA (US); Xinli E. Wu, Johnston, IA (US); Myoeng-Je Cho, Alameda, CA (US); Deping Xu, Johnston, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 395 days.

(21) Appl. No.: 12/649,673

(22) Filed: Dec. 30, 2009

(65) Prior Publication Data

US 2011/0160087 A1  Jun. 30, 2011

(51) Int. Cl.
- *C12N 15/84* (2006.01)
- *A01H 4/00* (2006.01)
- *A01H 1/04* (2006.01)

(52) U.S. Cl. ............... 800/294; 800/275; 800/320.1; 435/424; 435/430.1; 435/469

(58) Field of Classification Search .................. None
See application file for complete search history.

(56) References Cited

U.S. PATENT DOCUMENTS 5,024,944 A * 6/1991 Collins et al. ............... 800/294

OTHER PUBLICATIONS

Zhang et al. pp. 88-94 In: Plant Genetic Engineering: Towards the Third Millenium, A.D. Arencibia, ed., Elsevier Science B.V. (2000).*
Elliott et al. Plant Cell Reports 18: 707-714 (1999).*
Carvalho et al. Genetics and Molecular Biology 27(2): 259-269 (2004).*

* cited by examiner

*Primary Examiner* — David T Fox
(74) *Attorney, Agent, or Firm* — Alston & Bird LLP

(57) ABSTRACT

A method for increasing efficiency of germplasm screening for transformability may include providing a plurality of lines of plant target tissue to be transformed, characterizing each of the lines to provide characterization data, the characterization data comprises DNA or nucleic acid delivery technique response data and tissue culture response data, eliminating one or more of the plurality of lines based on the characterization data without performing transformation of the plurality of lines, such that a subset of the plurality of lines remains, and performing transformation experiments on the subset of the plurality of lines. The method may also include selecting a DNA or nucleic acid delivery technique protocol and a tissue culture protocol prior to the characterization.

21 Claims, 7 Drawing Sheets

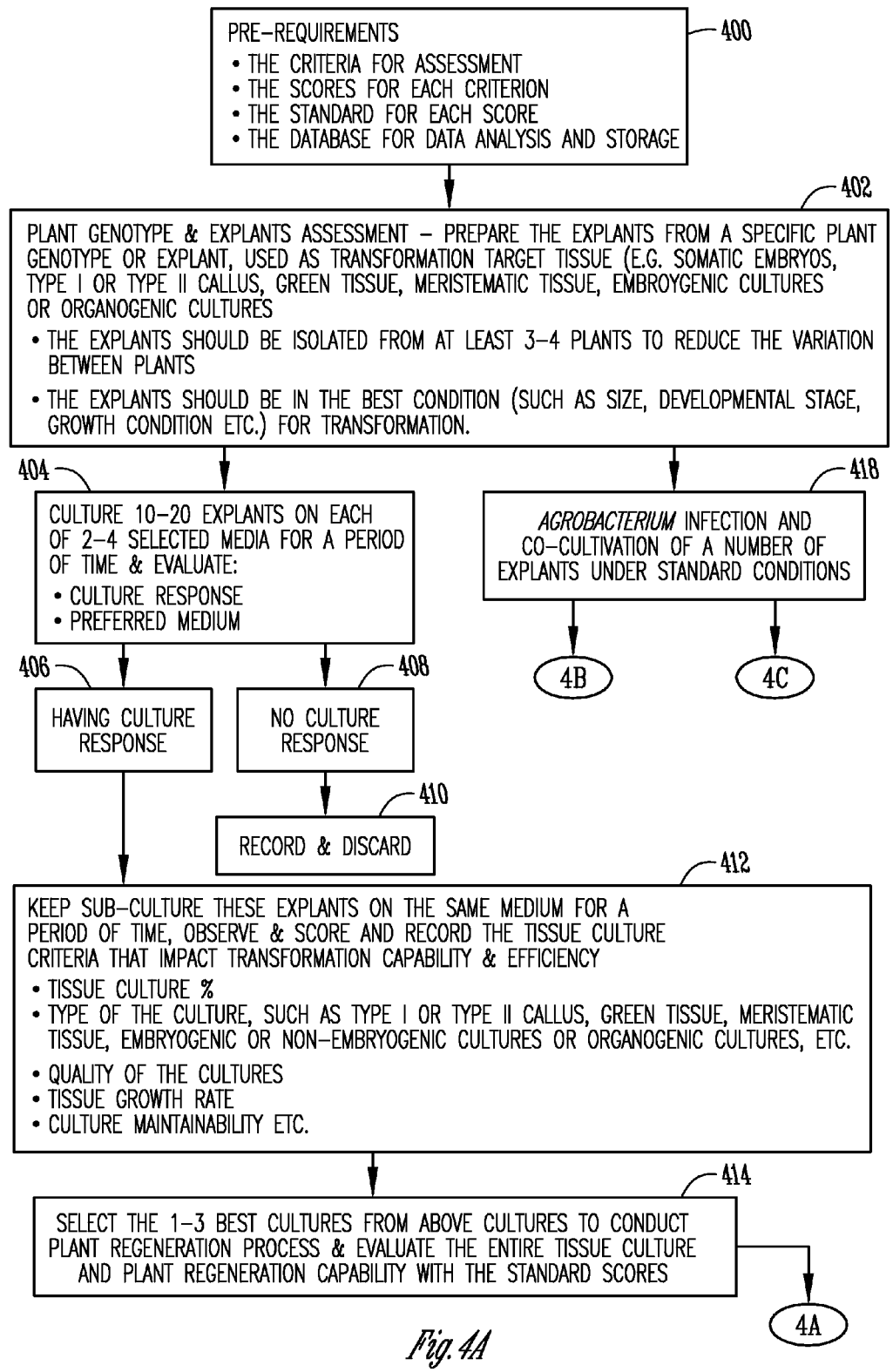

METHOD FOR INCREASING EFFICIENCY OF GERMPLASM SCREENING IN PLANT TRANSFORMATION

FIELD OF THE INVENTION

The present invention relates to the transformation of plants, and more particularly to germplasm screening.

BACKGROUND

The commercialization of germplasm and traits typically involves evaluating a number of lines of plants by screening these plants by transforming the plants and then collecting evaluation data for the transformed plants. The evaluation data is then used to identify which of the lines are of interest and suitable for subsequent commercialization or precommercialization activities. The evaluation data may include data regarding the efficacy of the transgene (how well the desired phenotype is expressed) and the overall agronomic performance of the line. Significant resources are expended in performing this process.

What is needed is a method which can reduce the time and costs associated with performing actual transformations.

SUMMARY OF THE INVENTION

A method for increasing efficiency of germplasm screening for transformability may include providing a plurality of lines of plant target tissue to be screened, characterizing each of the lines to provide characterization data, the characterization data comprises DNA delivery technique response data and tissue culture response data, eliminating one or more of the plurality of lines based on the characterization data without performing transformation of the plurality of lines, such that a subset of the plurality of lines remains, and performing transformation experiments on the subset of the plurality of lines. The method may also include selecting a DNA delivery technique protocol and a tissue culture protocol prior to the characterization.

BRIEF DESCRIPTION OF THE DRAWINGS

FIG. 4A-4B illustrate an example of a method for characterization of plant lines.

DETAILED DESCRIPTION

Methods are described which may be used to rapidly assess or predict the transformability of plant genotypes without actually performing stable transformations. Such methods are advantageous in improving overall efficiency of a germplasm screening process, reducing the amount of time for germplasm screening, reducing the number of experiments and workload or otherwise reducing or more efficiently using resources associated with germplasm screening.

Figure 1:
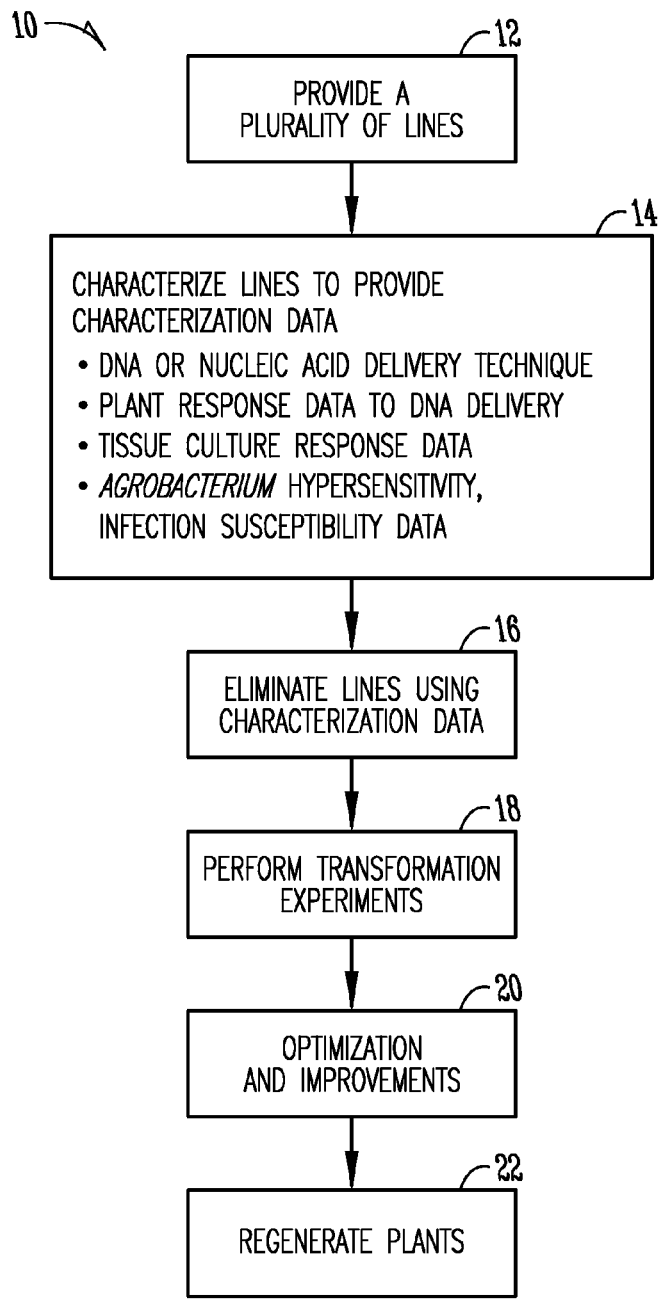
FIG. 1 is a flow chart illustrating a methodology for increasing the efficiency of germplasm screening.

In FIG. 1, an overview of the method 10 for increasing efficiency of germplasm screening is shown. In the method, one or more plant lines or plant genotypes are provided for characterization 12. These plant lines are then subjected one or more tests 14 to provide data which will allow for characterization of the plants suitability for transformation. The data which is useful in making this characterization includes, but is not limited to, the plant line's response to techniques for delivering genetic material (such as DNA delivery technique response data), the plant line's response to tissue culture conditions (such as tissue culture response data), and the plant line's susceptibility to *Agrobacterium* infection (such as *Agrobacterium* hypersensitivity and infection susceptibility data).

In step 16, one or more of the plurality of genetic lines are eliminated based, at least in part, on the characterization from step 14. This elimination may be accomplished without performing stable transformation experiments on the genetic lines which are eliminated. Instead, genetic lines are eliminated for which transformation experiments are likely to be ineffective based on the characterization data generated from the prior steps. After the elimination of one or more of the plurality of genetic lines, a subset of the plurality of lines remains, the subset containing candidate genetic lines for stable transformation.

In step 18, one or more of the remaining plant lines may be transformed with a gene of interest. Methods of transformation include, but are not limited to, the use of *Agrobacterium*, particle bombardment, electroporation, chemicals, microinjection, and viral transformation. The invention allows for a higher success rate in the transformation based on the characterization data which allows researchers to disregard plant lines which have a low likelihood of being successfully transformed.

In step 20, optimization and improvements may be made. This step may include any number of approaches to arrive at germplasm comprising the desired trait. Examples of these approaches include discarding transformed plant calli which show reduced growth, altering the media components, and/or tissue culture conditions, DNA delivery conditions to enhance callus growth, or other methods to increase the amount and/or quality of transformed calli.

In step 22, plants are regenerated from the transformed calli using standard techniques. Although not shown, additional characterization of the regenerated transformed plants may be performed. This characterization may include, but is not limited to, determining the stable transformation frequency, foreign DNA integration pattern, inserted DNA copy number and/or *Agrobacterium* backbone fragment integration if *Agrobacterium* is used for transformation etc. Some or all of these genetic lines shown to be capable of stable transformation through this process (step 10) may be used as the candidate lines for transformation optimization and/or selecting the top transformable lines by using this process with modified characterization criteria and/or different transformation conditions. In FIG. 1 note that some of the screening is performed without performing stable transformation experiments. Thus, the process shown in FIG. 1 is more efficient than processes which would perform a stable transformation experiment on every line. Although the data collected using the process of FIG. 1 would not be as complete as data acquired by performing a stable transformation experiment on every line, less time and resources are used in acquiring meaningful results which may be particularly advantageous when the screening process is used in a commercial context.

Example 1

Figure 2:
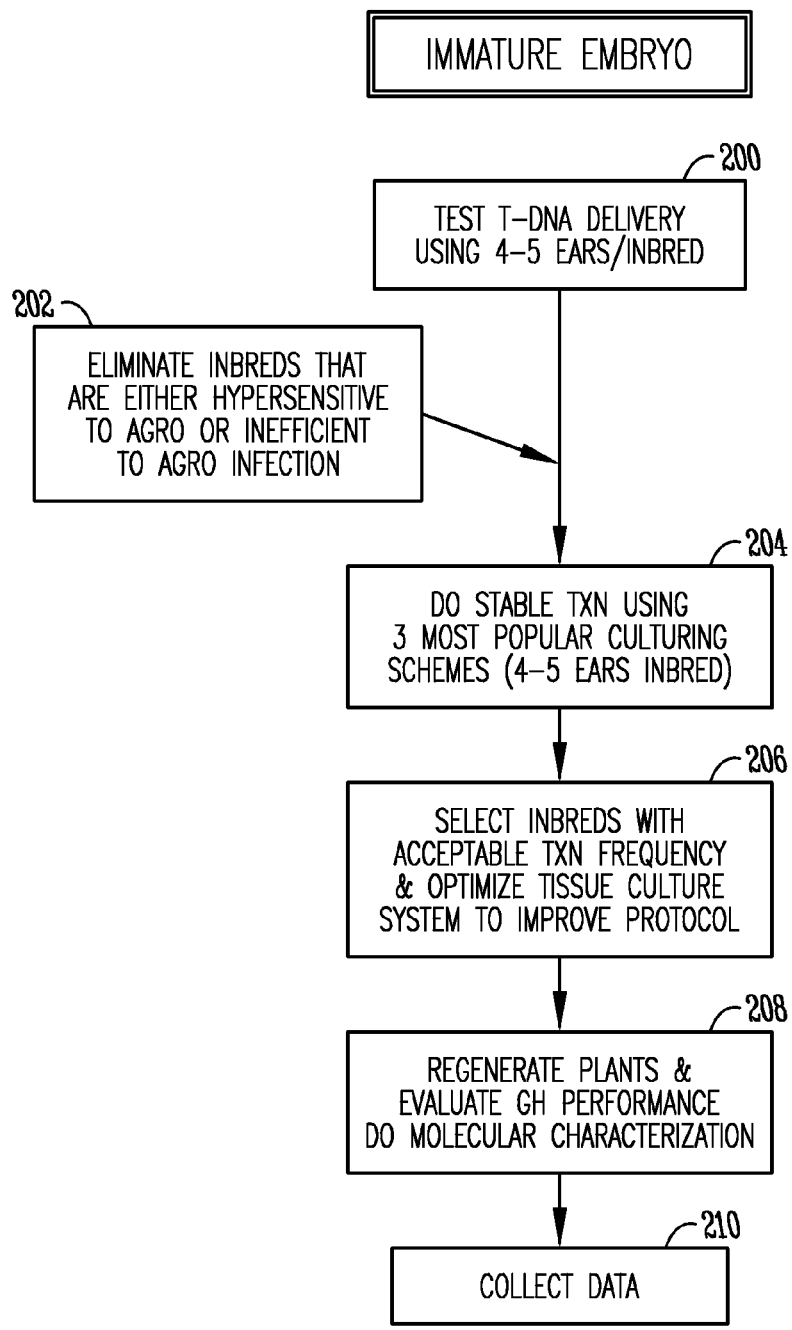
FIG. 2 is a flow chart illustrating a maize inbred transformability study performed using the germplasm screening methods of the invention (IEs: Immature Embryos).

A maize inbred transformability study was performed using the germplasm screening methods of the invention. FIG. 2 is a diagram showing the protocol used. This experiment shows the use of the methods of the present invention to increase the success while reducing the time and cost of transforming maize inbred plants using *Agrobacterium*-mediated transformation of immature embryos (IEs). A T-DNA delivery system was tested using embryos isolated from 4-5 ears per inbred 200.

Based on the data collected above, inbreds which demonstrated hypersensitivity to *Agrobacterium* or inefficient T-DNA delivery based on expression of the visible marker gene delivered by *Agrobacterium* were eliminated 202.

A stable transformation was performed 204 using 3 of the most promising culturing schemes (4-5 ears/inbred). The stable transformation resulted in a number of transformed inbred calli. Of these, inbreds with acceptable transformation frequency were selected 206. Additionally, routine optimizations in tissue culture materials and methodology were performed to encourage growth of the transformed calli for further improvement of transformation efficiencies.

Plants were regenerated from the calli 208 and green house performance of the transgenic plants was evaluated. Additionally, molecular characterization was performed. This data was collected and analyzed 210.

The process allows an acceptable and useful number of lines of interest to be identified in less time than methods which would call for additional experiments for every line and research time and expense in attempting to identify appropriate culturing schemes for every line.

Example 2

Figure 3:
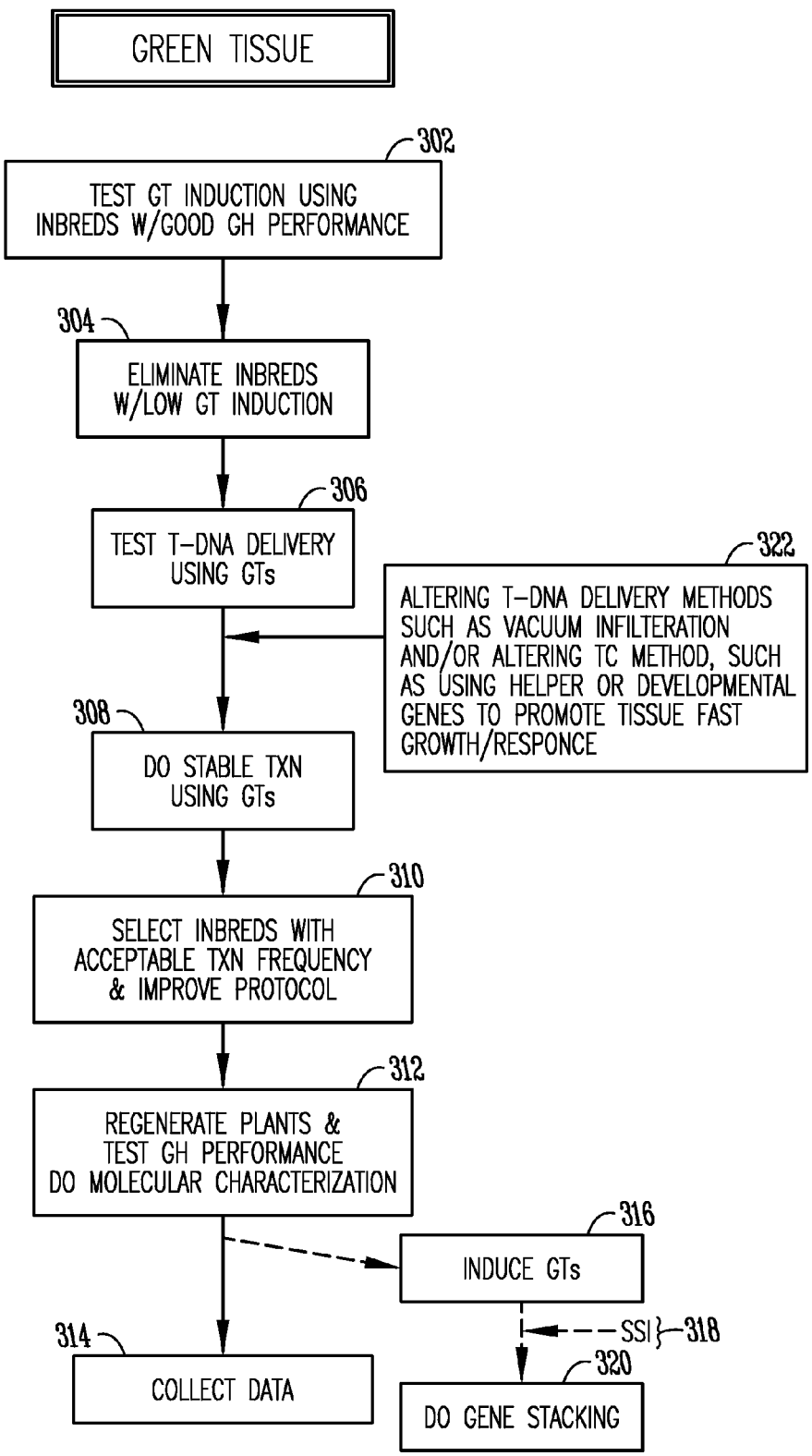
FIG. 3 is a flow chart illustrating another example of a maize inbred transformability study performed using the germplasm screening methods for green tissues (GTs).

Another maize inbred transformability study was performed using the germplasm screening methods of the invention. FIG. 3 is a diagram showing the protocol used. This experiment shows the use of the methods of the present invention to increase the success while reducing the time and cost of transforming maize inbred plants using *Agrobacterium*-mediated transformation of green regenerative tissue (green tissue: GT). Inbred lines exhibiting good greenhouse performance were used as the initial lines for characterization 302.

Green tissue induction was used to characterize the inbred lines. Based on the characterization data a subset of the inbred lines were eliminated from consideration due to low green tissue induction 304. The remaining inbred lines are used to test *Agrobacterium*-mediated T-DNA delivery 306. The inbred lines showing sufficient T-DNA delivery into the green tissues are selected for stable transformation 308. For the remaining inbred lines showing insufficient T-DNA delivery at step 306, alternative techniques may be used to promote T-DNA delivery such as vacuum infiltration or/and to promote fast green tissue growth with helper genes such as cell proliferation factor genes, including developmental genes, as shown in step 322.

The stable transformation resulted in a number of transformed green tissues. Of these, inbreds with acceptable transformation frequency were selected 310. Additionally, routine optimizations in tissue culture materials and methodology were performed to encourage growth of the transformed green tissues.

Plants were regenerated from the transformed green tissues 312 and greenhouse performance of the regenerated plants was evaluated. Additionally, molecular characterization was performed. These data were collected and analyzed 314.

Optionally, green tissue may be induced 316 and used for alternative transformation technology such as site-specific integration (SSI) mediated by a site-specific recombinase system, such as FLP/FRT, phiC31 integrase/att, lambda integrase/att, HK022 integrase/att, R/S, or Cre/Lox system 318. Through site-specific integration, multiple transgenes can be stacked at a pre-selected site in plant genome 320 resulting in inbred plant lines with multiple desirable traits.

Example 3

Figure 4B:
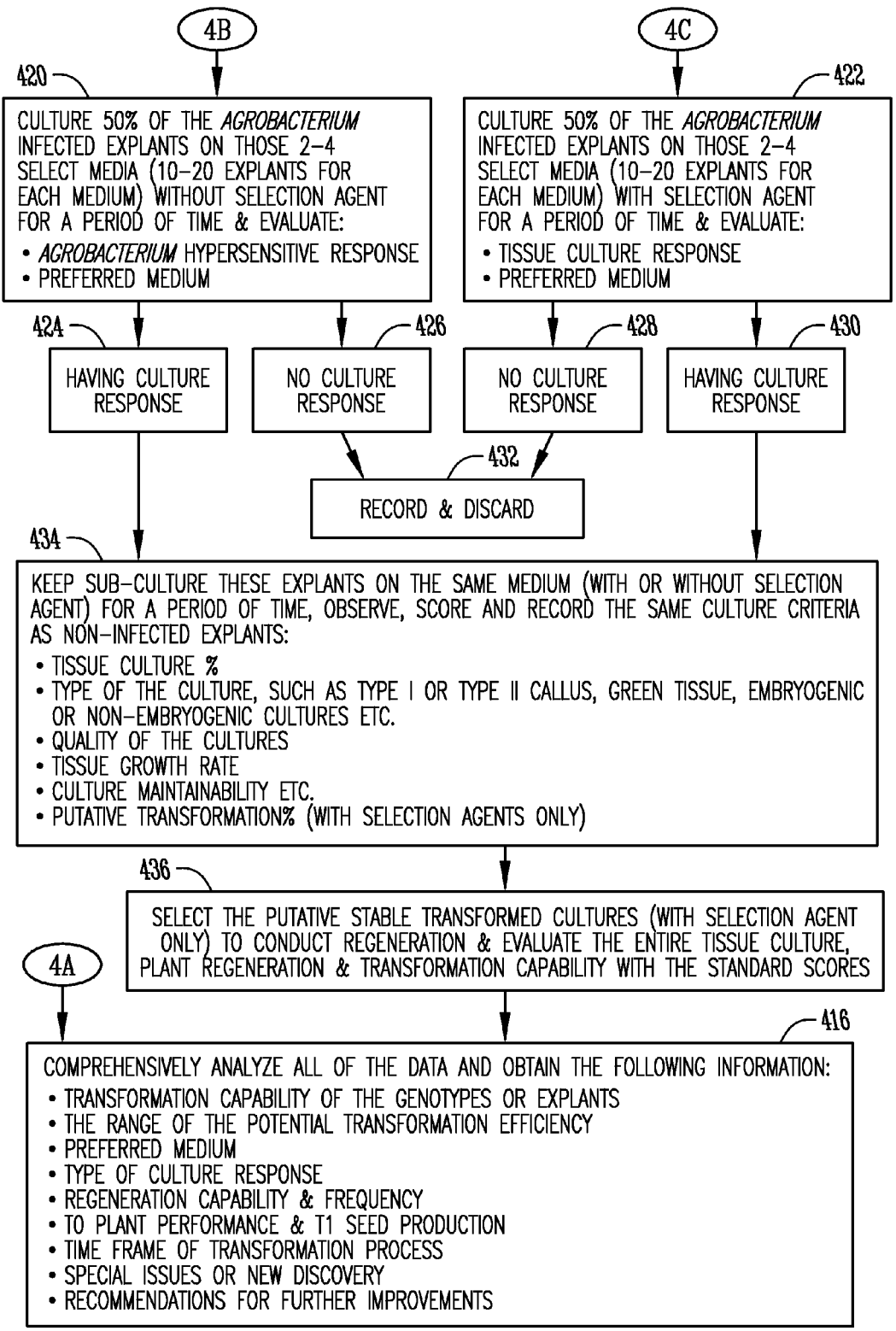

FIG. 4A-4B illustrates an example of a method for characterization of plant lines. FIG. 4A-4B illustrate an example of an assessment of plant genotypes and explants for transformation. In step 400, pre-requirements are described. The pre-requirements may include the criteria for assessment, the scores for each criterion, the standard for each score, and the database for data analysis and storage. In step 402, plant genotype and explant assessments are performed including preparation of the explants from specific plant genotype(s) or explants which will be used as transformation target tissue. Examples may include immature embryo, mature seed, green tissue, meristematic tissue or leaf tissue. Typically, the explants should be isolated from at least 3-4 plants to reduce the variation between plants. The explants should be in the best condition (such as size, developmental stage, growth conditions) for transformation.

In step 404, 10-20 explants are cultured on each of two to four selected media for a period of time. As part of the characterization data, culture response and the preferred medium are evaluated. In step 408, if there is no culture response, such information is recorded and the tissue is discarded and culture experiments are discontinued 410. In step 406, if there is a culture response, then testing proceeds as shown in step 412, the sub-cultures of these explants are kept on the same medium for a period of time. The tissue culture criteria that impact transformation capability and efficiency are observed, scored, and recorded and may be used as part of the characterization. Examples of such data may include the tissue culture percentage, the type of culture (such as Type I or Type II callus, green tissue, meristematic tissue, embryogenic or non-embryogenic cultures, organogenic cultures), the quality of the cultures, the tissue growth rate, the culture maintainability, or other criteria. Then in step 414 the best cultures (such as a subset of 1-3 cultures) are selected from the cultures derived from different explants, or from different media, or from using different culture conditions to conduct plant regeneration process and evaluate the entire tissue culture and plant regeneration capability. The plant regeneration capability may be characterized by any number of assays to provide standard scores.

In step 418, *Agrobacterium* infection and co-cultivation of a number of explants under standard conditions is performed. Any *Agrobacterium* transformation technique may be used in this step and the *Agrobacterium* plasmid typically contains at least one marker gene. Roughly half of the infected explants are grown under standard conditions without the use of selective media containing a selection agent 420 and roughly half of the explants are grown in the presence of selective media containing a selection agent 422. The selection agent in the selection media matches the marker gene on the *Agrobacterium* plasmid. Of the explants grown without the use of selective media, the explants which do not have a culture response (e.g. die or fail to grow) are deemed hypersensitive to *Agrobacterium* 426, data is recorded regarding the culture and the culture is discarded 432. For the explants grown in the presence of selective medium, the explants which demonstrate no culture response are deemed as having no tissue culture response 428, data regarding the explant is recorded and the culture is discarded 432. Of course other types of tissue culture response may be evaluated.

The explants which show a culture response to steps 420 and 422 are then subcultured on the same medium (that is with or without the selection agent) for a period of time 434. Various measurements are taken regarding the explants including the tissue culture percentage, the type of the culture (e.g. Type I or Type II callus, green tissue, meristematic tissue, embryogenic or non-embryogenic cultures, or organogenic cultures), the quality of the cultures, the tissue growth rate, and the culture maintainability. For those explants grown on selective media, a measure of transformation success such as the putative transformation frequency may be recorded as well.

The explants which putatively demonstrate stable transformation (based on the explants cultured in the presence of a selective agent) are then regenerated using standard techniques 436. The entire tissue culture is evaluated and various data is collected including the plant regeneration and transformation capability. Preferably standard scores are used in making these measurements.

The data collected in the process is then analyzed to characterize the inbred plant lines 416. This characterization may include measures such as the transformation capability of the genotypes and/or explants, the range of potential transformation frequency, preferred culture medium and type of culture response, the regeneration capability and frequency, the plant performance and seed production, and the time frame of the transformation process. Additionally, special issues or new discoveries may be noted as well as recommendations for future improvements regarding the lines.

Example 4

Figure 5A:
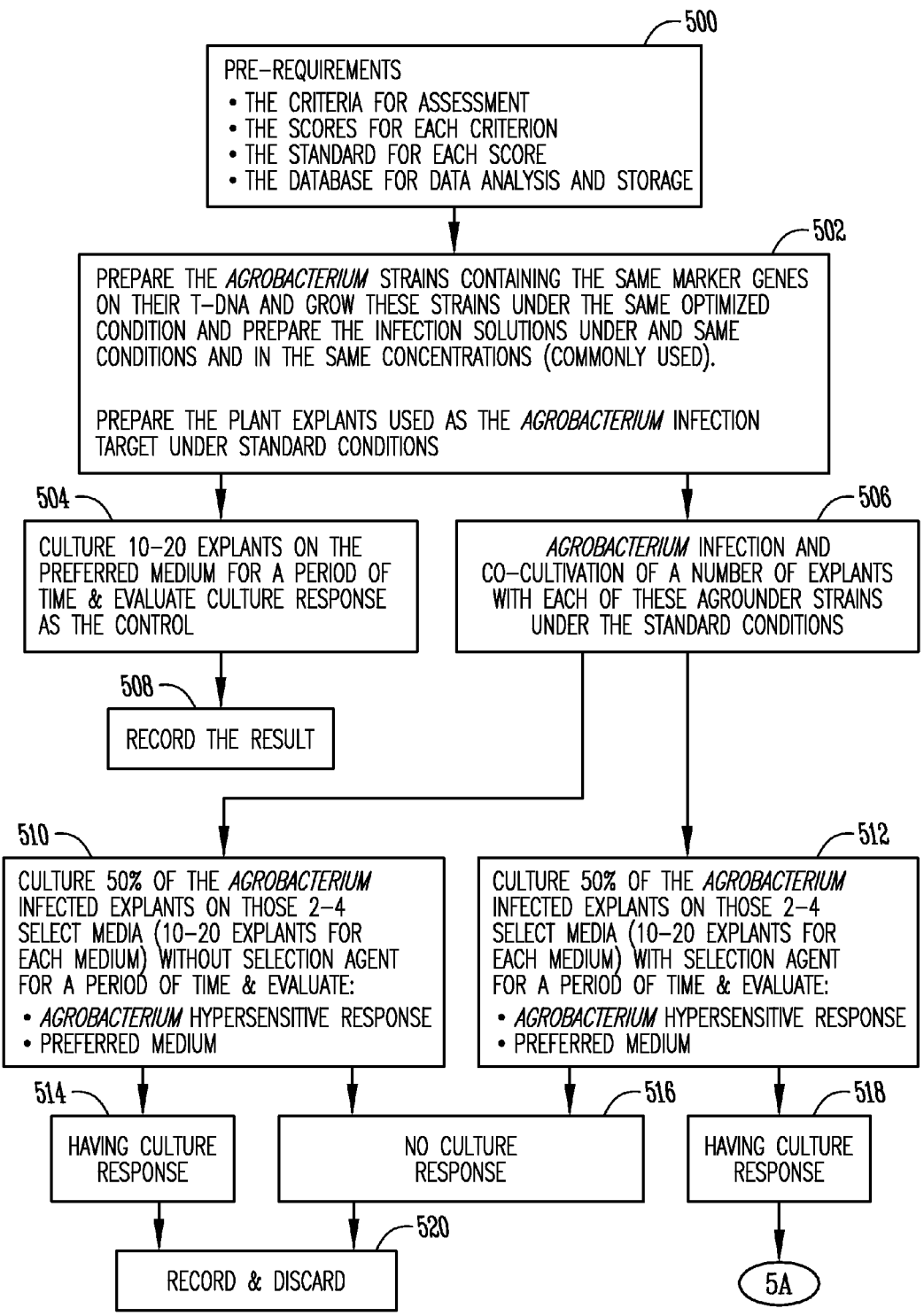
FIG. 5A-5B illustrate an example of a method for characterization of *Agrobacterium* strains.
Figure 5B:
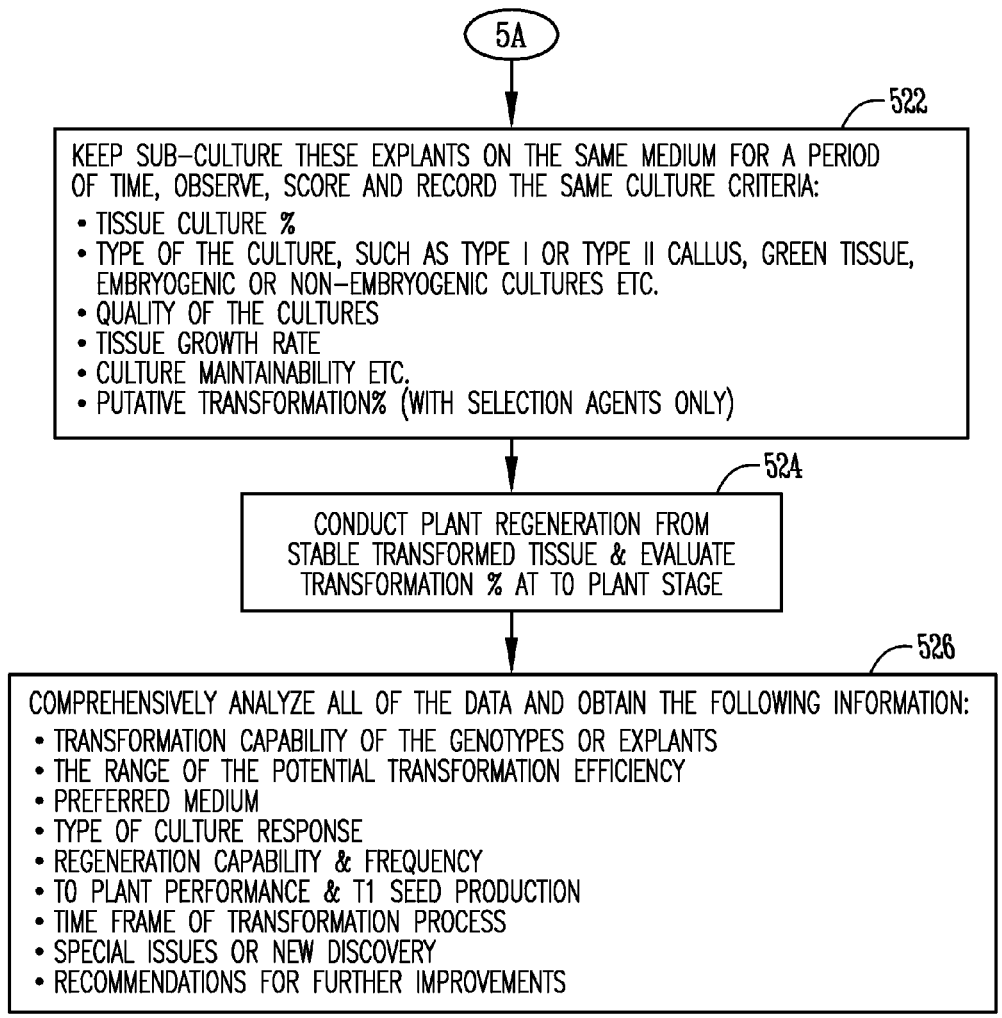

FIG. 5A-5B illustrates an example of a method for characterization of *Agrobacterium* for transformation. In step 500, pre-requirements are described. The pre-requirements may include the criteria for assessment, the scores for each criterion, the standard for each score, and the database for data analysis and storage. In step 502, *Agrobacterium* strains containing the same marker genes on their T-DNA are prepared and grown under the same optimized conditions. Infection solutions are prepared under the same conditions. Additionally, plant explants are prepared for use as *Agrobacterium* infection targets using standard conditions. The *Agrobacterium* strains can be different bacterium species, such as *Agrobacterium tumefaciens*, *Agrobacterium rhizogenes*, *Agrobacterium radiobacter* or *Agrobacterium rubi*; can be different *Agrobacterium* stains, such as octopine stains or nopaline strains etc.; can be *Agrobacterium* stains with modifications of their plasmid DNA and/or their chromosomal DNA.

A control is prepared using a number of explants (e.g. 10-20) which are grown on preferred medium for those explants for a period of time 504. The culture response of the explants and the data is regarded as a control 508.

A number of explants are infected by the tested *Agrobacterium* strains and co-cultivation of these explants with each of the *Agrobacterium* strains is performed under standard conditions 506 to produce infected explants.

Roughly 50 percent of the treated explants are grown on the preferred media for the explants without the use of a selection agent (typically around 10-20 explants per *Agrobacterium* strain tested) 510. The explants are grown for a period of time and data such as the culture response and hypersensitivity to the *Agrobacterium* are observed. The *Agrobacterium* used to infect the explants having no culture response 516 are regarded as evoking hypersensitivity to *Agrobacterium* and the data from the explants is recorded and the culture is discarded 520. The *Agrobacterium* used to infect explants having a culture response 514 are deemed as not provoking a hypersensitive response to *Agrobacterium* and the data from the explants is recorded and the culture is discarded 520.

Roughly another 50 percent of the treated explants are grown on preferred media in the presence of a selection agent corresponding to the selection marker gene from the *Agrobacterium* 512. Again, generally 10-20 explants are used for each *Agrobacterium* strain. The explants are cultured for a period time and the culture response is evaluated. For those explants showing no culture response 516, the *Agrobacterium* used to infect the explants is regarded as not being efficient at transformation. The data regarding these explants is recorded and the culture is discarded 520. The explants which show a culture response 518 are subjected to further study.

The explants are subcultured on the same medium for a period of time 522 and observations are made including scoring the explants and recording the culturing criteria. Information which is recorded may include tissue culture percentage, the type of the culture (such as Type I or Type II callus, green tissue, meristematic tissue, embroygenic or non-embryogenic cultures, or organogenic cultures), the quality of the cultures, the tissue growth rate, the culture maintainability, and the transformation percentage at tissue culture stage.

Tissue from the stably transformed explants is then regenerated into plants 524. Various measures are taken, including the transformation frequency, at the T0 plant stage.

Ultimately, the data collected throughout the experiment is analyzed to characterize the *Agrobacterium* strains suitability for plant transformation 526. This characterization may include measures such as the transformation capability of the *Agrobacterium* strains, the range of the potential transformation efficiency, the likelihood of generating a hypersensitive response, the timeframe of the transformation process. Additionally, special issues or new discoveries may be noted as well as recommendations for future improvements regarding the lines.

Although various examples have been provided, it is to be understood that the methodologies described herein may be applied to any number of types of plants. It is to be further understood, that the methodologies described herein may be applied to any number of types of tissue cultures, any number of types of delivery techniques, and any number of types of transformation experiments. It is to be appreciated that the specific protocols used may vary widely and that any number of protocols known in the art may be used. The present invention is not to be limited to or by the specific examples described herein.

What is claimed is:

1. A method for increasing efficiency of germplasm screening for transformability of a maize plant with agrobacterium, comprising:
   providing target tissue from a plurality of maize plant lines;
   characterizing each of the plant lines to provide characterization data, the characterization data comprises agrobacterium-mediated DNA or nucleic acid delivery technique response data and tissue culture response data under preferred tissue culture conditions;
   eliminating one or more of the plurality of maize plant lines based on the characterization data without performing stable transformation of the plurality of maize plant lines, such that a subset of the plurality of maize plant lines remains; and performing agrobacterium transformation experiments on the subset of the plurality of maize plant lines selected based on said characterization data.

2. The method of claim 1 wherein the DNA or nucleic acid delivery technique uses T-DNA delivery.

3. The method of claim 1 wherein the characterization data further comprises *Agrobacterium* sensitivity data.

4. The method of claim 3 wherein the *Agrobacterium* sensitivity data comprises *Agrobacterium* hypersensitivity data.

5. The method of claim 3 wherein the characterization data further comprises explant *Agrobacterium* susceptibility data.

6. The method of claim 5 further comprising selecting conditions for the *Agrobacterium*.

7. The method of claim 1 further comprising selecting conditions for the agrobacterium transformation experiments.

8. The method of claim 1 further comprising selecting conditions for the DNA or nucleic acid delivery technique.

9. The method of claim 1 further comprising selecting promoters or helper genes for use in the plant transformation.

10. The method of claim 1 further comprising regenerating maize plants from the subset of the plurality of maize lines.

11. The method of claim 1 wherein the characterization data further comprises callus response data.

12. The method of claim 1 further comprising selecting at least one of the maize plant lines after the performing of the agrobacterium transformation experiments.

13. The method of claim 1 wherein each of the target tissues from a plurality of maize plant lines is from the set consisting of somatic embryos, Type I or Type II callus, green tissue, meristematic tissue, embroygenic cultures and organogenic cultures.

14. A method for increasing efficiency of germplasm screening for maize plant transformability with agrobacterium, comprising:

providing target tissue from a plurality of maize plant lines to be transformed;

selecting an agrobacterium-mediated DNA or nucleic acid delivery technique protocol and a tissue culture protocol;

characterizing each of the maize plant lines to provide characterization data, wherein the characterization data comprises response data for the DNA or nucleic acid delivery technique protocol and the tissue culture protocol;

eliminating one or more of the plurality of maize plant lines based on the characterization data, without performing stable transformation of the plurality of maize plant lines, such that a subset of the plurality of maize plant lines remains; and performing agrobacterium transformation experiments on the subset of the plurality of maize plant lines selected based on said characterization data.

15. The method of claim 14 wherein the DNA or nucleic acid delivery technique protocol comprise a T-DNA delivery protocol.

16. The method of claim 14 wherein the characterization data further comprises *Agrobacterium* sensitivity data.

17. The method of claim 16 wherein the *Agrobacterium* sensitivity data comprises *Agrobacterium* hypersensitivity data.

18. The method of claim 16 wherein the characterization data further comprises *Agrobacterium* susceptibility data.

19. The method of claim 14 further comprising regenerating maize plants from the subset of the plurality of maize plant lines.

20. The method of claim 14 further comprising selecting at least one of the maize plant lines after the performing of the agrobacterium transformation experiments.

21. The method of claim 14 wherein each of the target tissues from a plurality of maize plant lines is from the set consisting of somatic embryos, Type I or Type II callus, green tissue, meristematic tissue, embroygenic cultures, and organogenic cultures.

* * * * *